United States Patent [19]
Nishihira et al.

[11] Patent Number: 5,534,648
[45] Date of Patent: Jul. 9, 1996

[54] PROCESS FOR CONTINUOUSLY PRODUCING DIMETHYL CARBONATE

[75] Inventors: Keigo Nishihira; Shinichi Yoshida; Shuji Tanaka, all of Ube, Japan

[73] Assignee: Ube Industries, Ltd., Yamaguchi, Japan

[21] Appl. No.: 345,568

[22] Filed: Nov. 28, 1994

[30] Foreign Application Priority Data

Nov. 30, 1993 [JP] Japan ................................. 5-299337
Dec. 3, 1993 [JP] Japan ................................. 5-303916

[51] Int. Cl.$^6$ ................................................. C07C 69/96
[52] U.S. Cl. ......................... 558/277; 558/260; 558/488
[58] Field of Search ................................... 558/277, 488

[56] References Cited

U.S. PATENT DOCUMENTS 4,353,843 10/1982 Doumaux, Jr. et al. ................ 558/488
4,879,401 11/1989 Doumaux, Jr. et al. ................ 558/488
5,162,563 11/1992 Nishihira et al. ..................... 558/277
5,214,185 5/1993 Nishihira et al. ..................... 558/277

Primary Examiner—José G. Dees
Assistant Examiner—Dwayne C. Jones
Attorney, Agent, or Firm—Burgess, Ryan and Wayne

[57] ABSTRACT

A process for producing dimethyl carbonate is carried out by a first step of catalytically reacting carbon monoxide with methyl nitrite to produce dimethyl carbonate; a second step of absorbing dimethyl carbonate contained in a gas fraction withdrawn from the first step by dimethyl oxalate; a third step of regenerating methyl nitrite by contacting nitrogen monoxide contained in a gas fraction withdrawn from the second step with a molecular oxygen-containing gas and methyl alcohol; a fourth step of collecting dimethyl carbonate by distilling a liquid fraction withdrawn from the second step; and a fifth step of producing and recovering methyl nitrite from a purge gas consisting of a minor portion of a gas fraction withdrawn from one of the second step and the third step by bringing the purge gas together with an ammonia-oxidation product gas into contact with methyl alcohol in a methyl nitrite-recovering column, to thereby produce and recover methyl nitrite contained in the recovering column with a high efficiency at a high level of safety.

20 Claims, 2 Drawing Sheets

PROCESS FOR CONTINUOUSLY PRODUCING DIMETHYL CARBONATE

BACKGROUND OF THE INVENTION

1. Field of the Invention

The present invention relates to a process for continuously producing dimethyl carbonate. More particularly, the present invention relates to an industrial process for continuously producing dimethyl carbonate in large scale by a catalytical reaction in gas phase of carbon monoxide with methyl nitrite in the presence of a solid catalyst, while effectively and safely recovering methyl nitrite and nitrogen monoxide from a purge gas withdrawn from a gas-circulating system for this process, and restricting a loss of carbon monoxide.

Dimethyl carbonate is a compound useful as a material for synthesizing aromatic polycarbonates, medicines and agricultural chemicals, and as a solvent.

2. Description of the Related Art

A conventional industrial process for producing dimethyl carbonate by a catalytical reaction in gas phase of carbon monoxide with methyl nitrite in the presence of a solid catalyst comprises, as disclosed in U.S. Pat. No. 5,214,185, a first step of catalytically reacting carbon monoxide with methyl nitrite in gas phase in the presence of a solid catalyst in a reactor to produce dimethyl carbonate; a second step of absorbing dimethyl carbonate produced in the first step by an absorbing medium consisting of dimethyl oxalate in a dimethyl carbonate-absorbing column (absorbing column), to provide a liquid fraction comprising dimethyl carbonate absorbed by dimethyl oxalate and a non-condensed gas fraction containing nitrogen monoxide; a third step of regenerating methyl nitrite by bringing nitrogen monoxide in the non-condensed gas fraction into contact with molecular oxygen and methyl alcohol in a methyl nitrite-regenerating column (regenerating column); and a fourth step of distil-collecting dimethyl carbonate from the liquid fraction produced in the second step and containing dimethyl oxalate in which dimethyl carbonate is absorbed, in an extract-distilling column and a dimethyl carbonate-distilling column, the reaction of carbon monoxide with methyl nitrite and the regeneration of methyl nitrite from nitrogen monoxide are carried out in accordance with the following chemical equations.

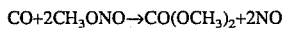

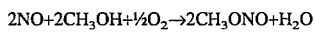

As the chemical equations clearly show, in the dimethyl carbonate-producing process, methyl nitrite and nitrogen monoxide are not consumed and serve as catalysts in theory. However, in practice, it cannot be avoided that they are partially lost due to the fact that portions thereof are dissolved in the liquid fraction from the second step and in the liquid fraction from the third step, and purged from the gas-circulating system for the process of the present invention through the first, second and third steps. Accordingly, the lost methyl nitrite and nitrogen oxides are compensated by adding methyl nitrite and NOx compound to the gas circulating system.

To compensate methyl nitrite and NOx, a NOx gas is produced by a reaction of sodium nitrite with an inorganic acid, for example, nitric acid or sulfuric acid, and mixed with the circulating gas and a molecular oxygen-containing gas, and the resultant mixed gas is fed into the regenerating column of the third step. This method of producing the NOx gas is simple and advantageous in the production of the NOx gas. However, to produce dimethyl carbonate on a large scale to utilize it for the production of aromatic polycarbonate resins or the like, the above-mentioned method is disadvantageous in that the starting materials are special, and sodium nitrate is produced as a by-product.

In another method of producing the NOx compounds, ammonia is oxidized with air. This method is disadvantageous in that a large amount of nitrogen contained in air accompanies the resultant NOx compounds. Therefore, when the ammonia oxidation product gas is used for the process for producing dimethyl carbonate, namely, the ammonia-oxidation product gas is introduced into the regenerating column of the third step, it is necessary to purge a portion of a circulating gas of the process in a large amount. In this case, methyl nitrite and nitrogen monoxide in the purge gas can be recovered by the method as disclosed in U.S. Pat. No. 4,879,401.

However, this recovering method is disadvantageous in that carbon monoxide contained in the purge gas is difficult to recover and thus the loss of carbon monoxide becomes very large.

SUMMARY OF THE INVENTION

An object of the present invention is to provide a process for continuously producing dimethyl carbonate by a catalytic reaction of methyl nitrile with carbon monoxide on a large industrial scale, while feeding nitrogen oxides necessary to regenerate methyl nitrite with a high efficiency.

Another object of the present invention is to provide a process for continuously producing dimethyl carbonate by a catalytic reaction of methyl nitrite with carbon monoxide on a large industrial scale, while feeding nitrogen oxides necessary to regenerate methyl nitrite at a high level of efficiency without increasing the loss of carbon monoxide.

Still another object of the present invention is to provide a process for continuously producing dimethyl carbonate by a catalytic reaction of methyl nitrite with carbon monoxide on a large industrial scale, while feeding nitrogen oxides necessary to regenerate methyl nitrite, recovering methyl nitrite and nitrogen monoxide contained in a purge gas discharged from the process, and preventing a by-production of nitric acid during the recovery step.

The above-mentioned objects can be attained by the process of the present invention for continuously producing dimethyl carbonate, which comprises a first step of preparing dimethyl carbonate by a catalytic reaction of carbon monoxide with methyl nitrite in gas phase in the presence of a solid catalyst in a reactor;

a second step of absorbing the dimethyl carbonate by an absorption medium comprising dimethyl oxalate in a dimethyl carbonate-absorbing column, to provide a liquid fraction containing dimethyl carbonate absorbed by the absorbing medium and a non-condensed gas fraction containing nitrogen monoxide;

a third step of regenerating methyl nitrite by bringing at least a major portion of the non-condensed gas fraction containing nitrogen monoxide into contact with molecular oxygen and methyl alcohol in a methyl nitrite-regenerating column, to provide a liquid fraction containing water dissolved in methyl alcohol and a regenerated gas fraction containing the regenerated methyl nitrite and nitrogen oxides at least a major portion of the regenerated gas fraction being recycled to the reactor of the first step;

a fourth step of collecting dimethyl carbonate by distilling the absorbing medium liquid fraction produced in the second step, in a distilling column; and a fifth step of producing and recovering methyl nitrite by bringing a purge gas consisting of a minor portion of the gas fraction withdrawn from one of the second step and the third step and a gas comprising an oxidation product of ammonia with a molecular oxygen-containing gas into contact with methyl alcohol in a methyl nitrite-recovering column, thereby to convert nitrogen oxides contained in the purge gas and the ammonia-oxidation product gas to methyl nitrite and to absorb methyl nitrite contained in the purge gas and regenerated by the above-mentioned conversion, by methyl alcohol.

DESCRIPTION OF THE PREFERRED EMBODIMENTS

Figure 1:
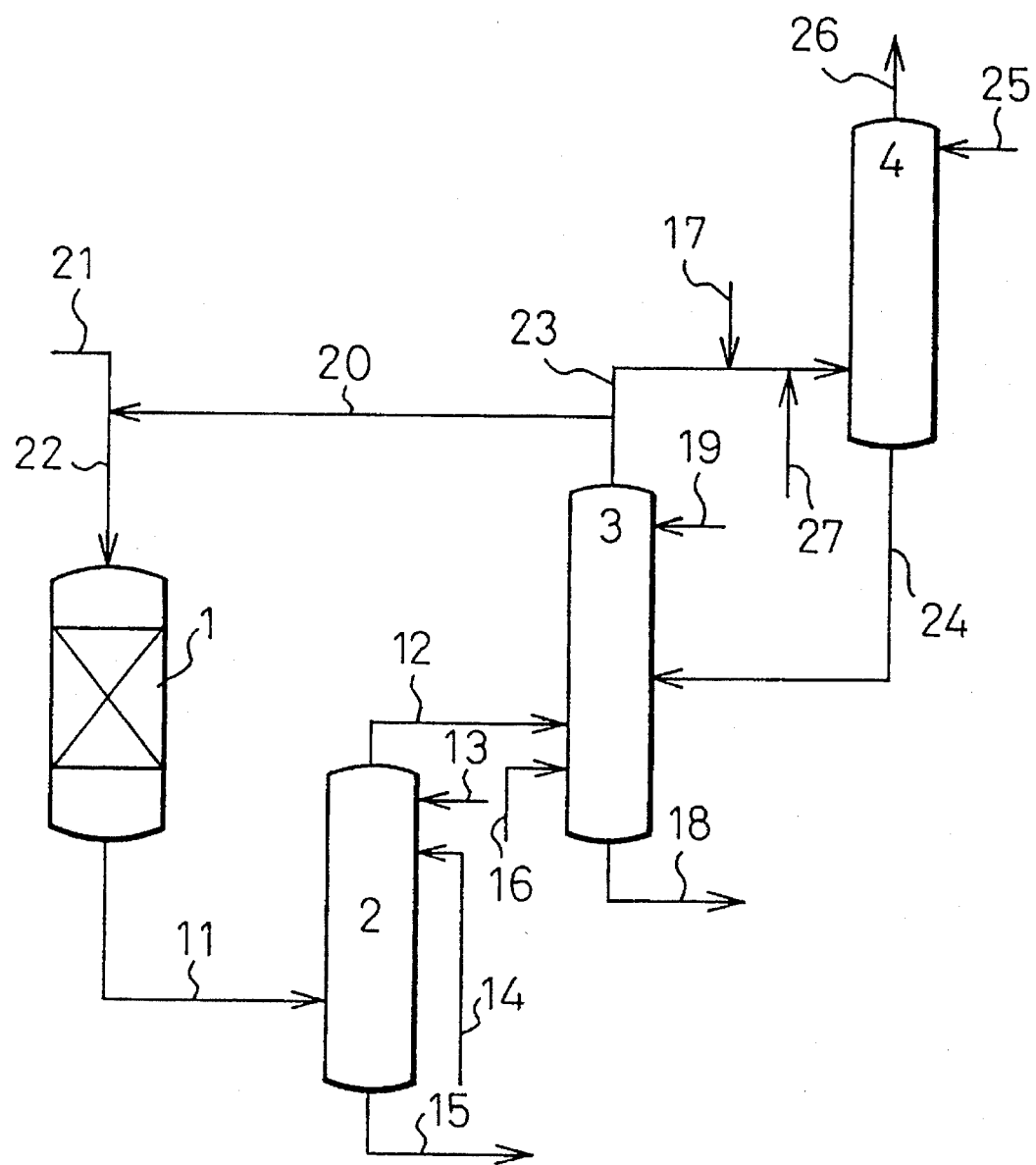
FIG. 1 is a flow sheet showing an embodiment of the process of the present invention.

First, the steps of the process of the present invention will be explained briefly below.

In the first step of the process of the present invention, a material gas containing carbon monoxide and methyl nitrite is introduced into a reactor packed with a solid catalyst in which a catalytical component comprises a platinum group metal element and/or a compound thereof and optionally an assistant catalytical component both carried on a carrier, to cause carbon monoxide to react with methyl nitrite in gas phase and to provide a reaction product gas containing the resultant dimethyl carbonate.

In the second step of the process of the present invention, the reaction product gas provided in the first step is introduced into a dimethyl carbonate-absorbing column (which will be referred to as an absorbing column hereinafter) and brought into contact with an absorbing medium consisting of dimethyl oxalate to provide a non-condensed gas fraction containing nitrogen monoxide produced as a by-product of the catalytical reaction of the first step, and a liquid fraction separated from the non-condensed gas fraction, and comprising dimethyl oxalate, dimethyl carbonate absorbed by dimethyl oxalate and methyl alcohol.

In the third step, at least a major portion of the non-condensed gas provided in the second step is introduced into a methyl nitrite-regenerating column, which will be referred to as a regenerating column hereinafter, and brought into contact with a molecular oxygen-containing gas and methyl alcohol which are also introduced into the regenerating column, to regenerate methyl nitrite from nitrogen monoxide contained in the non-condensed gas. The resultant gas fraction containing the regenerated methyl nitrite is recycled to the reactor for the first step.

In the fourth step, the dimethyl oxalate solution prepared in the second step and containing dimethyl carbonate and methyl alcohol is subjected to an extract-distilling procedure for removing methyl alcohol and then to a distilling procedure for collecting the target dimethyl carbonate.

In the process of the present invention, a gas circulation system is formed through the above-mentioned first, second and third steps. During the circulation, a by-product gas including, for example, carbon dioxide which is produced in the first step, is accumulated in the circulating gas and thus, the total amount of the circulating gas increases. This increase in the total amount of the circulating gas necessarily causes a portion of the circulating gas to be purged from the gas circulation system.

In the process of the present invention, a minor portion of the regenerated gas fraction withdrawn from the third step (regenerating column) or a minor portion of the non-condensed gas fraction withdrawn from the second step (absorbing column) is purged as a purge gas. The amount of the purge gas is established in response to the amount of the by-product gas accumulated in the gas circulation system.

In the process of the present invention portions of carbon monoxide and methyl nitrite, which are starting materials for the production of dimethyl carbonate, and a portion of nitrogen monoxide contained in the circulating gas are lost by the discharge of the purge gas. Also, portions of methyl nitrite and nitrogen monoxide are lost by discharging the liquid fraction from the second step (absorbing column) and/or by discharging the liquid fraction from the third step (regenerating column).

To compensate the loss of methyl nitrite and nitrogen oxides which are a regenerating source of methyl nitrite, a gas produced by oxidizing ammonia with air is fed into the fifth step so that an increase in loss of carbon monoxide is prevented.

In the fifth step of the process of the present invention, a purge gas consisting of a minor portion of a gas fraction withdrawn from one of the second step (absorbing column) and the third step (regenerating column) is introduced together with an ammonia-oxidation product gas into a methyl nitrite-producing and recovering column which will be referred to as a recovering column hereinafter. Also, methyl alcohol is fed into the recovering column of the fifth step.

In the fifth step (recovering column), the nitrogen oxides in the purge gas and the ammonia-oxidation product gas are brought into contact with methyl alcohol to regenerate methyl nitrite. Also, methyl nitrite regenerated by the above-mentioned step and methyl nitrite contained in the purge gas are absorbed by methyl alcohol. The resultant methyl alcohol solution containing methyl nitrite is recycled and reused in the third step (regenerating column).

The ammonia-oxidation product gas can be easily prepared by oxidizing ammonia with a molecular oxygen-containing gas, for example, air, at a low cost. The ammonia-oxidation product gas is particularly useful when a large amount of NOx is necessary.

The ammonia-oxidation product gas is prepared by using a certainly excessive amount of air, and thus contains a large amount nitrogen gas in addition to the NOx gas. Accordingly, if the ammonia-oxidation product gas is directly fed into the gas circulation system (the first, second and third steps), a large amount of the nitrogen gas is introduced into the gas circulation system. This causes the circulating gas to be purged in a very large amount from the gas circulation system. This results in an increased loss of carbon monoxide which is one of the staring materials for the process of the present invention.

Accordingly, in the process of the present invention, the ammonia-oxidation product gas is fed into the recovering column of the fifth step, which column is arranged outside of the gas circulation system (the first, second and third steps), and the nitrogen gas introduced together with the NOx gas into the fifth step is contained in the gas fraction produced in the fifth step and discharged as a waste gas from the fifth step. During the fifth step, the NOx compounds introduced into the recovering column, are converted to methyl nitrile. Also, the methyl nitrite present in the recovering column is absorbed by methyl alcohol, and the resultant solution of methyl nitrite in methyl alcohol is recycled to the third step (regenerating column).

The preparation of the ammonia-oxidation product gas can be effected by a conventional, industrial process for producing nitric acid. In this preparation, preferably air and ammonia are mixed with each other in a molar ratio of oxygen to ammonia ($O_2/NH_3$) of 0.5:1 to 5.0:1, preferably 0.8:1 to 3.0:1, and the mixture is brought into a solid catalyst containing platinum or iron and bismuth in gas phase so as to catalytically react ammonia with oxygen.

The first to fifth steps of the process of the present invention will be further explained in detail below.

First Step

In the first step of the process of the present invention, dimethyl carbonate is prepared by introducing a material gas containing carbon monoxide and methyl nitrite into a reactor packed with a solid catalyst comprising a catalytic platinum group metal element and/or compound and optionally an assistant catalytic component both carried on a carrier, so as to catalytically react carbon monoxide with methyl nitrite in gas phase.

The solid catalyst usable for the process of the present invention may be selected from those disclosed in, for example, U.S. Pat. No. 5,162,563, comprising a catalytic component comprising at least one member selected from elements and compounds of platinum group metals and optionally, an assistant catalytic component both carried on a carrier.

The platinum group metal elements and compounds usable for the present invention may be selected from palladium, platinum, iridium, ruthenium and rhodium elements and compounds thereof. The most preferred compound is palladium chloride.

The solid catalyst may comprise an assistant catalytic component carried on the carrier and comprising at least one compound of other metals than the platinum group metals, for example, copper, iron, bismuth and cerium.

The carrier usable for the present invention comprises at least one member selected from, for example, activated carbon, alumina, silica, diatomaceous earth, zeolite and clay minerals.

In the first step, carbon monoxide and methyl nitrite are usually diluted with an inert gas, for example, nitrogen gas or carbon dioxide gas which are inert to the catalytic reaction of the present invention, to provide a material gas. The material gas is fed to the reactor at a feeding rate suitable for causing the material gas to be remained in contact with the solid catalyst preferably for a time of 10 seconds or less, more preferably 0.2 to 5 seconds. The reactor for containing the solid catalyst is preferably selected from single tube-type reactors and multiple tube type reactors.

The concentration of methyl nitrite in the material gas is established in consideration of the reaction rate and safety thereof. To obtain a satisfactory reaction rate, the concentration of methyl nitrite is preferably 1% by volume or more, more preferably 1 to 25% by volume. However, since methyl nitrite is an explosive compound, it is not preferred that the concentration of methyl nitrite be too high. Usually, in the process of the present invention, the preferable concentration of methyl nitrite in the material gas is 3 to 25% by volume.

The concentration of carbon monoxide in the material gas is broadly variable. However, in the continuous process of the present invention, since a minor portion of the circulating gas is purged as mentioned above, an increase in the concentration of carbon monoxide results in an increase in amount of carbon monoxide discharged to the outside of the process system, and thus is not preferred in economical point of view. Accordingly, the industrially preferable concentration of carbon monoxide in the material gas is in the range of from 1 to 50% by volume, more preferably 5 to 30% by volume.

Usually, the catalytic reaction is carried out at a relatively low temperature, as long as the reaction rate at this temperature is satisfactory.

Preferably, the reaction temperature is in the range of from 50° to 200° C., more preferably from 80° to 150° C. Also, the reaction pressure is preferably in the range of from the ambient atmospheric pressure (0 kg/cm$^2$G) to 10 kg/cm$^2$G, more preferably 1 to 6 kg/cm$^2$G.

After the catalytic reaction is completed, a reaction product gas containing dimethyl carbonate, dimethyl oxalate, nitrogen monoxide, carbon dioxide, non-reacted carbon monoxide and methyl nitrite and an inert gas is delivered from the reactor.

The target dimethyl carbonate is collected by introducing the reaction product gas into an absorbing column for the second step, and absorbing dimethyl carbonate by dimethyl oxalate introduced into the absorbing column through an upper portion thereof.

Second Step

In the second step, dimethyl carbonate is collected from the reaction product gas by bringing the reaction product gas into contact with an absorbing medium consisting of dimethyl oxalate, in an absorbing column.

In the absorbing column, the feeding rate of dimethyl oxalate is variable depending on the amount of dimethyl carbonate contained in the reaction product gas and introduced into the absorbing column. Usually, dimethyl oxalate is preferably fed in an amount of 3 to 10 times, more preferably 4 to 6 times the weight of dimethyl carbonate fed into the absorbing column.

To effect the absorption of dimethyl carbonate with a high efficiency, the absorbing temperature is preferably low. However, if the absorbing temperature is too low, dimethyl oxalate is solidified and the necessary energy consumption for the absorption disadvantageously increases. Therefore, the absorption is carried out preferably at a temperature of 0° to 100° C., more preferably 30° to 80° C.

In the second step, an absorbing medium liquid fraction comprising dimethyl carbonate absorbed by dimethyl oxalate and a non-condensed gas fraction containing nitrogen monoxide are provided. At least a major portion of the non-condensed gas fraction withdrawn from the absorbing column contains small amounts of dimethyl carbonate and dimethyl oxalate. If dimethyl carbonate and dimethyl oxalate are fed into the third step, they are uselessly consumed in the third step. Therefore, a small amount of methyl alcohol is preferably fed into the absorbing column (the second step) through a top portion of the absorbing column so that they are recovered by methyl alcohol. Usually, methyl alcohol is fed preferably in an amount of 5 to 30% by weight, more preferably 10 to 20% by weight based on the amount of dimethyl carbonate contained in the reaction product gas.

Since the non-condensed gas contains, in addition to non-reacted carbon monoxide and methyl nitrite, a large amount of nitrogen monoxide produced in the first step, this nitrogen monoxide is used to regenerate methyl nitrite in the regenerating column for the third step.

The liquid fraction of the second step contains the target dimethyl carbonate dissolved in dimethyl oxalate, and is subjected to the fourth step.

Third Step

In the third step of the process of the present invention, methyl nitrite is regenerated by introducing the non-condensed gas into the regenerating column and bringing it into contact with a molecular oxygen-containing gas and methyl alcohol. The regenerating column is selected from packing columns, bubbling columns, spraying columns and tray columns which are all conventionally employed as a gas-liquid contact reaction apparatus.

The molecular oxygen-containing gas usable for the process of the present invention may be a pure oxygen gas, a mixed gas consisting of oxygen diluted with an inert gas, for example, nitrogen gas, or air.

In the third step, the molecular oxygen-containing gas is fed in an amount of 0.08 to 0.2 mole in terms of oxygen per mole of nitrogen monoxide introduced into the regenerating column. The molecular oxygen-containing gas and the non-condensed gas containing nitrogen monoxide are brought into contact with methyl alcohol at a temperature of 60° C. or less for a contact time of 0.5 to 2 seconds.

In the third step, methyl alcohol is fed in a necessary amount or more to produce methyl nitrite by the reaction of methyl alcohol with nitrogen dioxide and nitrogen monoxide. Usually, methyl alcohol is fed preferably in an amount of 2 to 5 moles per mole of nitrogen monoxide fed into the regenerating column.

In the process of the present invention, the methyl alcohol to be used in the regenerating column of the third step is supplied through two feeding lines. In the first feeding line, methyl alcohol is directly fed into a top portion of the regenerating column. In the second feeding line, methyl alcohol is fed into the recovering column of the fifth step in which methyl alcohol is brought into contact with the purge gas and the ammonia-oxidation product gas so that methyl alcohol absorbs methyl nitrite in this column, and the methyl nitrite-containing methyl alcohol is fed into a middle portion of the regenerating column. The proportion of the methyl alcohol fed through the first line to that through the second line is variable depending on the amount of the purge gas divided from the circulating gas. Preferably, 30 to 90% by weight, more preferably 50 to 80% by weight of the total methyl alcohol are fed directly into the top portion of the regenerating column through the first feeding line.

From the third step regenerating column, a liquid fraction is discharged. This liquid fraction comprises methyl alcohol containing water produced as a by-product of the regenerating reaction of methyl nitrite. The liquid fraction is subjected to a refining procedure of methyl alcohol by removing water. In this refining procedure, the content of water is reduced to a level of 2% by volume or less, preferably 0.2% by volume or less. The refined methyl alcohol is reused for the second step (absorbing column), the third step (regenerating column) and fifth step (recovering column).

Fourth Step

The liquid fraction withdrawn from the second step absorbing column and containing the target dimethyl carbonate dissolved in dimethyl oxalate is subjected to a fourth step to collect the target dimethyl carbonate.

In the fourth step, impurities having a low boiling temperature, for example, methyl alcohol and a small amount of methyl formate which is a by-product of the catalytic reaction, are removed by an extract-distilling procedure, and then the target dimethyl carbonate is collected by a distilling procedure.

Fifth Step

The production and recovery of methyl nitrite in the fifth step of the process of the present invention is carried out by feeding a purge gas withdrawn from one of the second step (absorbing column) and the third step (regenerating column), an ammonia-oxidation product gas for supplementing NOx compounds necessary to produce methyl nitrile and methyl alcohol into the recovering column so that the NOx compounds in the purge gas and the ammonia-oxidation product gas are brought into contact with methyl alcohol to produce methyl nitrite from the NOx compounds and to absorb methyl nitrite contained in the purge gas and the produced methyl nitrite, by methyl alcohol.

The methyl nitrite-recovering column for the fifth step may be selected from conventional gas-liquid contact types of absorbing columns, for example, packing columns, tray columns and bubbling columns.

The ammonia-oxidation product gas is fed together with the purge gas into the bottom portion of the recovering column. In this feeding operation, the ammonia-oxidation product gas and the purge gas may be separately fed into the recovering column. Preferably, they are mixed with each other and then the mixed gas is fed into the recovering column. As mentioned above, the ammonia-oxidation product gas is obtained by, for example, oxidizing ammonia with air, and the purge gas is divided from the gas fraction withdrawn from the second step or third step.

The amount of the purge gas from one of the second and third steps is variable depending on the total amount of by-product, for example, carbon dioxide accumulated in the gas circulation system. Preferably, the purge gas is fed in an amount of 0.1 to 30% by volume/hr, more preferably 0.1 to 20% by volume/hr, based on the volume of the gas withdrawn from the absorbing column of the second step, or from the regenerating column of the third step.

Also, the ammonia-oxidation product gas introduced into the recovering column preferably contains the NOx compounds in an amount of 0.1 to 30 molar %/hr, based on the total molar amount of methyl nitrite and nitrogen monoxide contained in the gas withdrawn from the absorbing column of the second step or from the regenerating column of the third step.

If necessary, a molecular oxygen-containing gas similar to that introduced into the regenerating column of the third step is fed into the recovering column. The amount of the molecular oxygen is established in consideration of the content of nitrogen monoxide in the purge gas.

In the fifth step, methyl alcohol is fed into the recovering column through a top portion thereof to regenerate methyl nitrite from nitrogen monoxide in the purge gas, to convert NOx compounds in the ammonia-oxidation product gas to methyl nitrite, and absorbing methyl nitrite present in the recovering column by methyl alcohol.

In the fifth step, methyl alcohol is fed preferably in a molar amount of 5 to 200 times, more preferably 20 to 50 times, the total molar amount of nitrogen monoxide and methyl nitrite in the purge gas and the NOx compounds in the ammonia-oxidation product gas. To enhance the absorbing efficiency of methyl nitrite by methyl alcohol, it is preferable that methyl alcohol be cooled and fed at a temperature of 20° C. or less, more preferably 10° C. or less, into the recovering column.

The process of the present invention will be explained next in detail with reference to FIGS. 1 and 2 which are respectively a flow sheet of an embodiment of the process of the present invention.

Figure 2:
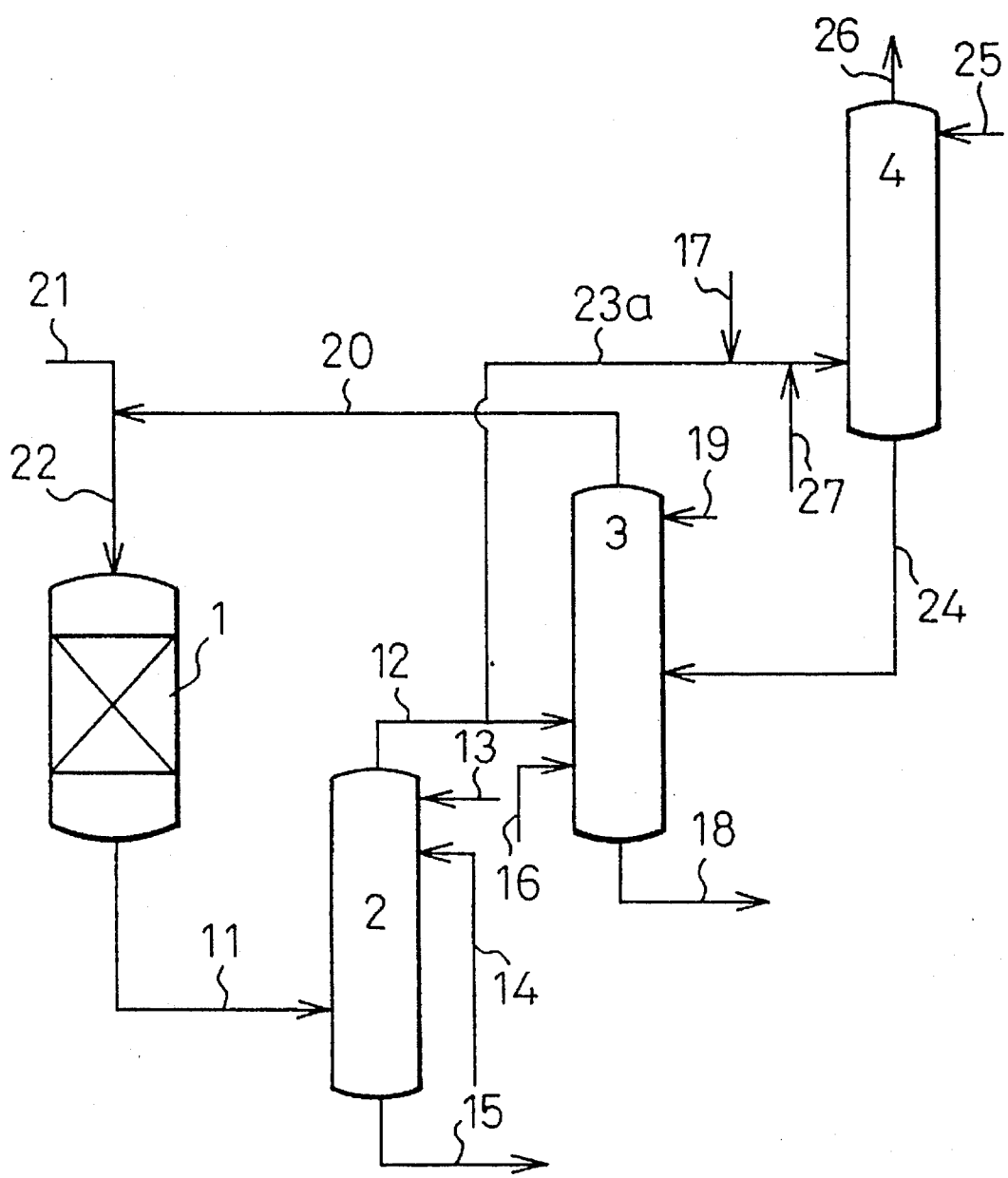
FIG. 2 is a flow sheet showing another embodiment of the process of the present invention.

Referring to FIGS. 1 and 2, a material gas comprising carbon monoxide, methyl nitrite and nitrogen monoxide is pressurized by a gas-circulator 1 (not shown in FIG. 1) located in a conduit line 20 and then introduced into a top portion of a multiple-tube type reactor equipped with reaction tubes packed with a platinum group metal-containing solid catalyst, through a conduit 22. In this reactor 1, a catalytic reaction of carbon monoxide with methyl nitrite is carried out in the gas phase. A reaction product-containing gas passed through the catalyst layers in the reaction tubes is withdrawn from the bottom portion of the reactor 1 and then introduced into a dimethyl carbonate-absorbing column 2 through a conduit 11.

In the absorbing column 2, the introduced gas containing dimethyl carbonate is brought into contact with methyl alcohol introduced through a conduit 13 and with dimethyl oxalate introduced through a conduit 14, and dimethyl carbonate in the introduced gas is absorbed and collected by dimethyl oxalate. A resultant liquid fraction containing dimethyl carbonate, dimethyl oxalate and methyl alcohol is withdrawn from a bottom portion of the absorbing column 2 through a conduit 15, and fed into a refining apparatus (not shown in FIG. 1) which may be a conventional apparatus, for example, a distilling column, for collecting dimethyl carbonate from the liquid fraction.

Also, a non-condensed gas fraction separated from the liquid fraction and containing non-reacted carbon monoxide, methyl nitrite and nitrogen monoxide produced, as a by-product, by the catalytic reaction is withdrawn from the top portion of the absorbing column 2 through a conduit 12.

In the conduit 12, at least a major portion of the non-condensed gas is mixed with a molecular oxygen-containing gas introduced through a conduit 16, and the resultant mixed gas is introduced into a column 3 for regenerating methyl nitrite and brought into contact in counter current with methyl alcohol introduced into a top portion of the regenerating column 3 through a conduit 19. During the contact, methyl nitrite is regenerated in the column 3.

At least a major portion of the resultant regenerated methyl nitrite-containing gas is withdrawn from a top portion of the regenerating column 3 through a conduit 20, and introduced, together with fresh carbon monoxide fed through a conduit 21, into the reactor 1 through the conduit 22. A by-product produced in the regenerating column 3 and consisting of water is withdrawn in the state of a solution in methyl alcohol from the bottom portion of the regenerating column 3 through a conduit 18. The methyl alcohol solution of water is subjected to a procedure for removing water from the solution, for example, a distilling procedure. The recovered methyl alcohol is recycled into the dimethyl carbonate-absorbing column 2 through the conduit 13, into a methyl nitrite-regenerating column 3 through a conduit 19 and/or into a methyl nitrite-recovering column 4 through a conduit 25, and re-used in each column.

In an embodiment shown in FIG. 1, a minor portion of the regenerated methyl nitrite-containing gas fraction produced in and withdrawn from the regenerating column 3 through a conduit 20 is purged through a conduit 23 and introduced into the column 4 for producing and recovering methyl nitrite.

In another embodiment shown in FIG. 2, a minor portion of a gas fraction produced in and withdrawn from the absorbing column 2 through a conduit 12 is withdrawn through a conduit 23a and introduced into the methyl nitrite-recovering column 4.

The purged portion of the gas fraction withdrawn from one of the regenerating column 3 of the third step and the absorbing column 2 of the second step will be referred to as a purge gas hereinafter.

Referring to FIGS. 1 and 2, the purge gas is mixed with an ammonia-oxidation product gas fed through a conduit 17 and containing NOx compounds, and the mixed gas is introduced into the bottom portion of the methyl nitrite-recovering column 4. If necessary, a molecular oxygen-containing gas is fed into the conduit 23 or 23a through a conduit 27 and mixed with the purge gas and the ammonia-oxidation product gas. Also, methyl alcohol is fed into the top portion of the recovering column 4 through the conduit 25. The introduced mixed gas is brought into contact countercurrently with methyl alcohol to convert nitrogen oxides contained in the purge gas and the ammonium-oxidation product gas to methyl nitrite. In the recovering column 4, methyl nitrite contained in the purge gas and the produced methyl nitrite are absorbed by methyl alcohol to provide a solution of methyl nitrite in methyl alcohol.

A liquid fraction consisting of the methyl alcohol solution containing methyl nitrite is withdrawn from the bottom portion of the recovering column 4 through a conduit 24 and then introduced into a middle portion of the regenerating column 3 of the third step. A gas fraction formed in the recovering column 4 and containing non-consumed portions of the purge gas, the ammonia-oxidation product gas and optionally the molecular oxygen-containing gas and a small amount a by-product gas, is discharged from the top portion of the recovering column 4 through a conduit 26.

EXAMPLES

The present invention will be further explained by the following specific examples.

In the examples, the space time yield (STY) in kg/m³·hr of dimethyl carbonate was calculated in accordance with the following equation (I):

$$STY(kg/m^3 \cdot hr) = a(b \times \theta) \qquad (I)$$

wherein θ represents a catalytic reaction time in hours of carbon monoxide with methyl nitrite in a reaction tube, a represents a weight in kg of the resultant dimethyl carbonate during the catalytic reaction time θ, and b represents a volume in m³ of a solid catalyst present in the reaction tube.

Example 1

Preparation of dimethyl carbonate

A multiple tube type reactor made from a stainless steel and equipped with 20 reaction tubes each having an inside diameter of 27 mm and a length (height) of 3 m was packed with 34.0 liters of a solid catalyst as disclosed in U.S. Pat. No. 5,162,563, in the form of pellets each having a diameter of 4 mm and a length of 6 mm and comprising palladium chloride and cupric chloride carried on a carrier consisting of activated carbon available under the Trademark of Shirasagi from Takeda Yakuhin K.K. Catalyst layers were formed in the reaction tubes. The reactor was further equipped with a jacket surrounding a shell of the reactor, through which jacket a heating medium flows.

A material gas comprising 20.0% by volume of carbon monoxide, 10.0% by volume of methyl nitrite, 4.0% by volume of nitrogen monoxide, 7.0% by volume of methyl alcohol, 1.0% by volume of carbon dioxide, and 58.0% by volume of nitrogen was pressurized by a gas compressor to a pressure of 4.02 kg/cm$^2$, pre-heated at a temperature of about 90° C. in a heat exchanger, and then fed into a top portion of the reactor at a feeding rate of 6.80 Nm$^3$/hr under a pressure of 4.02 kg/cm$^2$G at a feeding rate of 136 Nm$^3$/hr while maintaining the temperature of the center portions of the catalyst layers at a level of about 125° C. by circulating hot water through the jacket, to cause carbon monoxide to catalytically react with methyl nitrite.

In this reaction, the space time yield (STY) of dimethyl carbonate was 342 kg/m$^3$·hr.

The reaction product-containing gas passed through the catalyst layers was withdrawn from the reactor and introduced into a bottom portion of an absorbing column consisting of a Pole ring packing type gas-liquid contact absorbing apparatus having an inside diameter of 300 mm and a length (height) of 5 m. Also, methyl alcohol was introduced at a feeding rate of 3.6 liters/hr into the top of the absorbing column and dimethyl oxalate was introduced into a middle portion of the absorbing column through an inlet located 1000 mm below the top of the column at a feeding rate of 50.0 kg/hr, so that the reaction product-containing gas was brought into contact countercurrently with the introduced methyl alcohol and dimethyl oxalate at a column top temperature of 35° C. and at a column bottom temperature of 55° C. As a result, a liquid fraction was obtained in an amount of 65.8 kg/hr from the bottom of the absorbing column. The liquid fraction comprised 77.6% by weight of dimethyl oxalate, 17.3% by weight of dimethyl carbonate, 4.2% by weight of methyl alcohol, 0.1% by weight of methyl formate and 0.3% by weight of methyl nitrite.

Also, a non-condensed gas fraction was withdrawn at a flow rate of 132.6 Nm$^3$/hr from the top portion of the absorbing column. The withdrawn non-condensed gas contained methyl nitrite in a lower concentration than that in the material gas. Therefore, the non-condensed gas was subjected to a methyl nitrite-regenerating procedure (the third step).

The non-condensed gas was mixed with 1.54 Nm$^3$/hr of oxygen gas, and the resultant mixed gas was introduced into the regenerating column consisting of a gas-liquid contact-absorbing apparatus having an inside diameter of 300 mm and a length (height) of 6.4 m. The introduced mixed gas was brought into contact countercurrently with methyl alcohol introduced at a flow rate of 20 liter/hr into the top portion of the regenerating column, at a column top temperature of 30° C. and at a column bottom temperature of 40° C., to regenerate methyl nitrite. Simultaneously, a methyl alcohol solution containing methyl nitrite and withdrawn from the methyl nitrite-recovering column (the fifth step) was fed at a feeding rate of 14 liter/hr into a middle portion of the regenerating column.

In the regenerating column, a liquid fraction comprising a by-product consisting of water and dissolved in methyl alcohol and a gas fraction containing the regenerated methyl nitrite were provided.

The gas fraction was withdrawn at a flow rate of 132.7 Nm$^3$/hr from the top portion of the regenerating column. The gas fraction comprised 17.6% by volume of carbon monoxide, 10.3% by volume of methyl nitrite, 7.1% by volume of methyl alcohol, 4.1% by volume of nitrogen monoxide, 1.1% by volume of carbon dioxide and 59.5% by volume of nitrogen. A portion of the withdrawn fraction was purged in an amount of 400N liter/hr, as a purge gas, and the remaining major portion of the withdrawn gas fraction was recycled into the reactor.

The purge gas was mixed with 1.37 Nm$^3$/hr of an ammonia-oxidation product gas comprising 4.1% by volume of nitrogen monoxide, 5.7% by volume of nitrogen dioxide, 1.1% by volume of oxygen, 1.5% by volume of water and 87.6% by volume of nitrogen. The ammonia-oxidation product gas was prepared by the process mentioned hereafter.

The mixed gas was introduced into the bottom portion of a methyl nitrite-recovering column consisting of a gas-liquid contacting apparatus having an inside diameter of 70 mm and a length (height) of 1200 mm, and brought into contact countercurrently with methyl alcohol cooled to a temperature of 10° C. and introduced in an amount of 14.0 liter/hr into the top portion of the methyl nitrite-recovering column, to convert the NOx compounds to methyl nitrite and to absorb methyl nitrite present in the recovering column by methyl alcohol. A resultant liquid fraction contained 4.3% by weight of methyl nitrite dissolved in methyl alcohol. The liquid fraction was withdrawn from the bottom portion of the recovering column. Also, a gas fraction produced in the recovering column was withdrawn in a flow rate of 1.5 Nm$^3$/hr from the top portion of the column. The withdrawn gas fraction comprised 530 ppm of NOx, 1330 ppm of methyl nitrite, 4.7% by volume (7.5 N liter/hr) of carbon monoxide.

After the purge gas was divided, the remaining major portion of the gas fraction from the regenerating column (the third step) in an amount of 132.3 m$^3$/hr was pressurized by the above-mentioned gas compressor, and added with 3.3 Nm$^3$/hr of carbon monoxide and 0.3 Nm$^3$/hr of nitrogen. The resultant mixed gas comprising 20.0% by volume of carbon monoxide, 10.0% by volume of methyl nitrite, 4.0% by volume of nitrogen monoxide, 7.0% by volume of methyl alcohol, 1.0% by volume of carbon dioxide and 58.0% by volume of nitrogen, was introduced into the reactor.

A liquid fraction withdrawn in an amount of 24 liter/hr from the regenerating column contained 12.6% by weight of water dissolved in methyl alcohol. This liquid fraction was distilled to remove water, and then reused as a methyl alcohol source for the regenerating column (the third step), the recovering column (the fifth step) and optionally the absorbing column (the second step).

The target dimethyl carbonate was collected at an amount of 11.2 kg/hr from the liquid fraction withdrawn in an amount of 65.8 kg/hr from the absorbing column (the second step), by distilling the liquid fraction.

Preparation of ammonia-oxidation product gas

A mixed gas comprising 192 N liter/hr of ammonia gas and 1490 N liter/hr of air was preheated at a temperature of 100° C. by a preheater and then fed into a reactor made from a stainless steel, having an inside diameter of 30 mm and containing therein three platinum-ruthenium catalyst nets. The temperature of the reaction portion of the reactor was controlled to a level of 800° to 850° C. by using an electric furnace arranged outside of the reactor. Ammonia was oxidized with oxygen in air. The resultant ammonia-oxidation product gas contained 4.1% by volume of nitrogen monoxide, 5.7% by volume of nitrogen dioxide, 1.1% by volume of oxygen, 1.5% by volume of water and 87.6% by weight of nitrogen. This ammonia-oxidation product gas was used in Example 1 and Comparative Example 1.

Comparative Example 1

The same procedures as in Example 1 were carried out to produce dimethyl carbonate in a space time yield (STY) of 342 kg/m$^3$·hr in the reactor (the first step), to absorb the dimethyl carbonate by dimethyl oxalate in the absorbing column (the second step). Thereafter, the ammonia-oxidation product gas was fed into the regenerating column in the manner described below to regenerate methyl nitrite.

A non-condensed gas withdrawn from the absorbing column (the second step) was mixed in an amount of 132.6 Nm$^3$/hr with 1.37 Nm$^3$/hr of the ammonia-oxidation product gas comprising 4.1% by volume of nitrogen monoxide, 5.7% by volume of nitrogen dioxide, 1.1% by volume of oxygen, 1.5% by volume of water, and 87.6% by volume of nitrogen, and then with 1.54 Nm$^3$/hr of oxygen gas. The ammonia-oxidation product gas was used to supplement NOx compounds. The mixed gas was introduced into the bottom portion of the regenerating column. Also, methyl alcohol was introduced in an amount of 20 liter/hr into the top portion of the regenerating column. The mixed gas was brought into contact countercurrently with methyl alcohol at a column top temperature of 30° C. and at a column bottom temperature of 40° C., to regenerate methyl nitrite. Simultaneously, 14 liter/hr of a methyl alcohol solution containing methyl nitrite and withdrawn as a liquid fraction from the recovering column (the fifth step) was fed into a middle portion of the regenerating column.

A gas fraction was withdrawn in an amount of 133.9 Nm$^3$/hr from the regenerating column. This gas fraction comprised 17.5% by volume of carbon monoxide, 10.2% by volume of methyl nitrite, 4.1% by volume of nitrogen monoxide, 1.1% by volume of carbon dioxide, 7.1% by volume of methyl alcohol and 60.0% by volume of nitrogen.

To control the content of nitrogen in the gas fraction, a minor portion of the gas fraction was purged in an amount of 1.96 Nm$^3$/hr. The purge gas was mixed with 110 N liter/hr of air. The mixed gas was fed into the bottom portion of the recovering column in the same manner as in Example 1. Simultaneously, methyl alcohol cooled to a temperature of 10° C. was fed in an amount of 14 liter/hr into the top portion of the recovering column. The mixed gas was brought into contact countercurrently with methyl alcohol, to convert nitrogen monoxide contained in the purge gas to methyl nitrite and to absorb methyl nitrite contained in the purge gas and the produced methyl nitrite by methyl alcohol. The resultant liquid fraction of the recovering column contained 6.9% by weight of methyl nitrite. This liquid fraction was withdrawn from the bottom portion of the recovering column, and fed into the middle portion of the regenerating column. A waste gas fraction produced in the recovering column was withdrawn in an amount of 1.64 Nm$^3$/hr from the top portion thereof. This waste gas fraction contained 500 ppm of Nox, 1200 ppm of methyl nitrite, and 20.9% by volume (324 N liter/hr) of carbon monoxide.

After dividing the purge gas, 132.0 Nm$^3$/hr of the remaining major portion of the gas fraction from the regenerating column was pressurized by the above-mentioned gas compressor and mixed with 3.6 Nm$^3$/hr of carbon monoxide and with 0.3 Nm$^3$/hr of nitrogen. The resultant mixed gas comprising 20.0% by volume of carbon monoxide, 10.0% by volume of methyl nitrite, 4.0% by volume of nitrogen monoxide, 7.0% by volume of methyl alcohol, 1.0% by volume of carbon dioxide and 58.0% by volume of nitrogen, was introduced into the reactor.

Other procedures than those mentioned above were the same as in Example 1.

The compositions of the purge gases and the gas fractions (waste gases) discharged from the recovering column in Example 1 and Comparative Example 1 are shown in Table 1.

TABLE 1

| | Composition of purge gas | | | | Composition of gas fraction (waste gas) discharged from recovering column | | | |
|---|---|---|---|---|---|---|---|---|
| Example No. | Total amount of purge gas (N liter/hr) | CO (N liter/hr) | MN (N liter/hr) | NO (N liter/hr) | Total amount of gas fraction (N liter/hr) | CO (N liter/hr) | MN (N liter/hr) | NO (N liter/hr) |
| Example | 400 | 70.5 | 41.1 | 16.6 | 1500 | 70.5 | 2.0 | 0.8 |
| Comparative Example | 1961 | 342.2 | 199.7 | 80.7 | 1640 | 342.2 | 2.0 | 0.8 |

Note:
CO . . . carbon monoxide
MN . . . methyl nitrite
NO . . . nitrogen monoxide

Example 2

Preparation of dimethyl carbonate

A multiple tube type reactor made from a stainless steel and equipped with 20 reaction tubes each having an inside diameter of 27 mm and a length (height) of 3 m was packed with 34.0 liters of a solid catalyst as disclosed in U.S. Pat. No. 5,162,563, in the form of pellets each having a diameter of 4 mm and a length of 6 mm and comprising palladium chloride and cupric chloride carried on a carrier consisting of activated carbon available under the Trademark of Shirasagi from Takeda Yakuhin K.K. Catalyst layers were formed in the reaction tubes. The reactor was further equipped with a jacket surrounding a shell of the reactor, through which jacket a heating medium flows.

A material gas comprising 20.0% by volume of carbon monoxide, 10.0% by volume of methyl nitrite, 4.0% by volume of nitrogen monoxide, 7.0% by volume of methyl alcohol, 1.0% by volume of carbon dioxide, and 58.0% by volume of nitrogen was pressurized by a gas compressor to a pressure of 4.02 kg/cm$^2$, pre-heated at a temperature of about 90° C. in a heat exchanger, and then fed into a top portion of the reactor at a feeding rate of 6.80 Nm$^3$/hr under a pressure of 4.02 kg/cm$^2$G at a feeding rate of 136 Nm$^3$/hr while maintaining the temperature of the center portions of the catalyst layers at a level of about 125° C. by circulating hot water through the jacket, to cause carbon monoxide to catalytically react with methyl nitrite.

In this reaction, the space time yield (STY) of dimethyl carbonate was 342 kg/m$^3$·hr.

The reaction product-containing gas passed through the catalyst layers was withdrawn from the reactor and introduced into a bottom portion of an absorbing column consisting of a Pole ring packing type gas-liquid contact absorbing apparatus having an inside diameter of 300 mm and a length (height) of 5 m. Also, methyl alcohol was introduced at a feeding rate of 3.6 liters/hr into the top of the absorbing column and dimethyl oxalate was introduced into a middle portion of the absorbing column through an inlet located 1000 mm below the top of the column at a feeding rate of 50.0 kg/hr, so that the reaction product-containing gas was brought into contact countercurrently with the introduced methyl alcohol and dimethyl oxalate at a column top temperature of 35° C. and at a column bottom temperature of 55° C. As a result, a liquid fraction was obtained in an amount of 65.8 kg/hr from the bottom of the absorbing column. The liquid fraction comprised 78.0% by weight of dimethyl oxalate, 16.9% by weight of dimethyl carbonate, 4.2% by weight of methyl alcohol, 0.1% by weight of methyl formate and 0.3% by weight of methyl nitrite.

Also, a non-condensed gas fraction was withdrawn at a flow rate of 132.1 Nm$^3$/hr from the top portion of the absorbing column.

The withdrawn non-condensed gas comprised 17.6% by volume of carbon monoxide, 5.5% by volume of methyl nitrite, 8.8% by volume of nitrogen monoxide, 1.1% by volume of carbon dioxide, 7.2% by volume of methyl alcohol, and 59.7% by volume of nitrogen. A portion in an amount of 400 N liter/hr of the withdrawn non-condensed gas was divided as a purge gas.

The purge gas was mixed with 1.37 Nm$^3$/hr of an ammonia-oxidation product gas prepared by the procedures as mentioned below and comprising 4.1% by volume of nitrogen monoxide, 5.7% by volume of nitrogen dioxide, 1.1% by volume of oxygen, 1.5% by volume of water and 87.6% by volume of nitrogen.

The mixed gas was introduced into the bottom portion of a recovering column consisting of a gas-liquid contacting apparatus having an inside diameter of 70 mm and a length (height) of 1200 mm. Simultaneously, methyl alcohol cooled to a temperature of 10° C. was introduced in an amount of 14.0 liter/hr into the top portion of the recovering column. In this column, the mixed gas was brought into contact countercurrently with methyl alcohol, to convert NOx compounds to methyl nitrite and absorb methyl nitrite present in the recovering column by methyl alcohol.

A liquid fraction prepared in the recovering column containing 4.5% by weight of methyl nitrite and 0.22% by weight of nitric acid dissolved in methyl alcohol. The liquid fraction was withdrawn from the bottom portion of the recovering column and fed into a middle portion of a regenerating column. The amount of nitric acid corresponded to 5 molar % of the NOx compounds introduced into the recovering column. A waste gas fraction was discharged in an amount of 1.5 Nm$^3$/hr from the top portion of the recovering column. The withdrawn waste gas fraction contained 530 ppm of NOx, 1330 ppm of methyl nitrite, 4.7% by volume (7.5 N liter/hr) of carbon monoxide.

The non-condensed gas withdrawn from the absorbing column had a lower concentration of methyl nitrite than that in the material gas. Accordingly, the non-condensed gas was subjected to a regeneration of methyl nitrite in a regenerating column.

The non-condensed gas in an amount of 132.2 Nm$^3$/hr was mixed with 1.54 Nm$^3$/hr of oxygen gas, and the resultant mixed gas was introduced into a bottom portion of the regenerating column consisting of a gas-liquid contact-absorbing apparatus having an inside diameter of 300 mm and a length (height) of 6.4 m. Simultaneously, methyl alcohol was fed in an amount of 20 liter/hr into a top portion of the regenerating column. The mixed gas was brought into contact in counter current with methyl alcohol, at a column top temperature of 30° C. and at a column bottom temperature of 40° C., to regenerate methyl nitrite. Simultaneously, a methyl alcohol solution containing methyl nitrite and withdrawn from the methyl nitrite-recovering column (the fifth step) was fed in an amount of 14 liter/hr into a middle portion of the regenerating column.

In the regenerating column, a liquid fraction comprising a by-product consisting of water and dissolved in methyl alcohol and a gas fraction containing the regenerated methyl nitrite were provided.

The gas fraction was withdrawn in an amount of 132.4 Nm$^3$/hr from the top portion of the regenerating column.

The withdrawn gas fraction was compressed by the above-mentioned gas compressor and then mixed with 3.3 Nm$^3$/hr of carbon monoxide and 0.3 Nm$^3$/hr of nitrogen. The resultant mixed gas comprised 20% by volume of carbon monoxide, 10.0 by volume of methyl nitrite, 4.0% by volume of nitrogen monoxide, 7.0% by volume of methyl alcohol, 1.0% by volume of carbon dioxide and 58.0% by volume of nitrogen. The mixed gas was recycled to the reactor.

The liquid fraction of the regenerating column was withdrawn in an amount of 25 liter/hr from the bottom portion of the regenerating column. The withdrawn liquid fraction contained 12.5% by volume of water dissolved in methyl alcohol. This liquid fraction was subjected to distillation to remove water and then reused as a methyl alcohol source for the regenerating column.

Also, the liquid fraction withdrawn from the absorbing column was in an amount of 65.8 kg/hr, and the target dimethyl carbonate was continuously collected in an amount of 11.2 kg/hr from the liquid fraction by distillation thereof.

Preparation of ammonia-oxidation product gas

A mixed gas comprising 192 N liter/hr of ammonia gas and 1490 N liter/hr of air was preheated at a temperature of 100° C. by a preheater and then fed into a reactor made from a stainless steel, having an inside diameter of 30 mm and containing therein three platinum-ruthenium catalyst nets. The temperature of the reaction portion of the reactor was controlled to a level of 800° to 850° C. by using an electric furnace arranged outside of the reactor. Ammonia was oxidized with oxygen in air. The resultant ammonia-oxidation product gas contained 4.1% by volume of nitrogen monoxide, 5.7% by volume of nitrogen dioxide, 1.1% by volume of oxygen, 1.5% by volume of water and 87.6% by weight of nitrogen. This ammonia-oxidation product gas was used in Example 2 and Example 3.

Example 3

The same procedures as in Example 2 were carried out to produce dimethyl carbonate in a space time yield (STY) of 342 kg/m$^3$·hr in the reactor (the first step), to absorb the dimethyl carbonate by dimethyl oxalate in the absorbing column (the second step). Thereafter, the ammonia-oxidation product gas was fed into the regenerating column in the manner described below to regenerate methyl nitrite.

A non-condensed gas was withdrawn in an amount of 132.1 Nm³/hr from the absorbing column (the second step).

Since the non-condensed gas had a lower concentration of methyl nitrite than that in the material gas, methyl nitrite was regenerated from the non-condensed gas in a regenerating column. Also, since a portion of methyl nitrite was absorbed by the absorbing medium, a certain amount of NOx was added thereto.

Namely, the non-condensed gas was mixed with 1.54 Nm³/hr of oxygen gas, the resultant mixed gas was introduced into the bottom portion of the regenerating column. Simultaneously, 20 liter/hr of methyl alcohol was fed into the top portion of the regenerating column.

The mixed gas was brought into contact counter-currently with methyl alcohol at a column top temperature of 30° C. and at a column bottom temperature of 40° C., to regenerate methyl nitrite. Simultaneously, 14 liter/hr of a methyl alcohol solution containing methyl nitrite and withdrawn as a liquid fraction from the recovering column (the fifth step) was fed into a middle portion of the regenerating column.

A gas fraction was withdrawn in an amount of 132.7 Nm³/hr from the regenerating column. This gas fraction comprised 17.6% by volume of carbon monoxide, 10.3% by volume of methyl nitrite, 7.1% by volume of methyl alcohol, 4.1% by volume of nitrogen monoxide, 1.1% by volume of carbon dioxide and 59.5% by volume of nitrogen. A minor portion of the withdrawn gas fraction was purged in an amount of 400 N liter/hr. The purge gas was mixed with 1.37 Nm³/hr of the same ammonia-oxidation product gas as mentioned above. The mixed gas was subjected to the same methyl nitrite-recovering procedure as in Example 2, to convert NOx compounds in the mixed gas to methyl nitrite and to absorb methyl nitrite present in the recovering column by methyl alcohol. The liquid fraction withdrawn from the bottom portion of the recovering column contained 4.3% by weight of methyl nitrite and 0.39% by weight of nitric acid. The liquid fraction was fed into a middle portion of the regenerating column. The amount of nitric acid corresponded to 10 molar % of the NOx compounds contained in the mixed gas introduced into the recovering column. A waste gas fraction was discharged in an amount of 1.5 Nm³/hr from a top portion of the recovering column. This waste gas fraction contained 530 ppm of NOx, 1330 ppm of methyl nitrite, and 4.7% by volume (7.5 N liter/hr) of carbon monoxide.

After dividing the purge gas, 132.3 Nm³/hr of the remaining major portion of the gas fraction from the regenerating column was pressurized by the above-mentioned gas compressor and mixed with 3.3 Nm³/hr of carbon monoxide and with 0.3 Nm³/hr of nitrogen. The resultant mixed gas comprising 20.0% by volume of carbon monoxide, 10.0% by volume of methyl nitrite, 4.0% by volume of nitrogen monoxide, 7.0% by volume of methyl alcohol, 1.0% by volume of carbon dioxide and 58.0% by volume of nitrogen, was introduced into the reactor.

The liquid fraction withdrawn from the regenerating column was in an amount of 24 liter/hr and contained 12.6% by weight of water dissolved in methyl alcohol. Water was removed from the liquid fraction by distilling it. The water-removed methyl alcohol was re-used in the regenerating column.

Also, the liquid fraction withdrawn from the absorbing column was in an amount of 65.8 kg/hr and the target dimethyl carbonate was continuously collected in an amount of 11.2 kg/hr by distilling the liquid fraction.

The compositions of the methyl alcohol liquid fraction withdrawn from the recovering column in Example 2 and Example 3 are shown in Table 2.

TABLE 2

| | Item Composition of methyl alcohol liquid fraction withdrawn from recovering column | | |
|---|---|---|---|
| Example No. | Content of MN (wt %) | Content of nitric acid (wt %) | Molar ratio of nitric acid to NOx (molar %) |
| Example 2 | 4.5 | 0.22 | 5 |
| Example 3 | 4.3 | 0.39 | 10 |

Note: MN ... methyl nitrite

In the continuous process of the present invention for producing dimethyl carbonate by a catalytic reaction of carbon monoxide with methyl nitrite in the presence of a solid catalyst, a purge gas consisting of a portion of a gas fraction withdrawn from an absorbing column for absorbing the target dimethyl carbonate by dimethyl oxalate or from a regenerating column for regenerating methyl nitrite is mixed with an ammonia-oxidation product gas and fed into a methyl nitrite-recovering column. The utilization of the ammonia-oxidation product gas to supplement NOx compound to the process effectively enables, as Tables 1 and 2 clearly indicate, methyl nitrite and nitrogen monoxide in the purge gas to be recovered with a high efficiency without increasing the loss of carbon monoxide and nitrogen oxides, while preventing the by-production of nitric acid and nitric acid esters. Also, by the process of the present invention, dimethyl carbonate can be produced on a large industrial scale with a high efficiency with a reduced risk of explosion.

We claim:

1. A process for continuously producing dimethyl carbonate comprising:

a first step of preparing dimethyl carbonate by a catalytic reaction of carbon monoxide with methyl nitrite in a gas phase in the presence of a solid catalyst in a reactor;

a second step of absorbing the dimethyl carbonate by an absorption medium comprising dimethyl oxalate in a dimethyl carbonate-absorbing column, to provide a liquid fraction containing dimethyl carbonate absorbed by the absorbing medium and a non-condensed gas fraction containing nitrogen monoxide;

a third step of regenerating methyl nitrite by bringing at least a major portion of the non-condensed gas fraction containing nitrogen monoxide into contact with molecular oxygen and methyl alcohol in a methyl nitrite-regenerating column, to provide a liquid fraction containing water dissolved in methyl alcohol and a regenerated gas fraction containing the regenerated methyl nitrite and nitrogen oxides, at least a major portion of the regenerated gas fraction being recycled to the reactor of the first step;

a fourth step of collecting dimethyl carbonate by distilling the absorbing medium liquid fraction produced in the second step, in a distilling column; and a fifth step of producing and recovering methyl nitrite by bringing a purge gas consisting of a minor portion of the gas fraction withdrawn from one of the second step and the third step and a gas comprising an oxidation product of ammonia with a molecular oxygen-containing gas into contact with methyl alcohol in a molar amount of 5 to 200 times the total molar amount of nitrogen monoxide and methyl nitrite contained in the purge gas and NOx contained in the ammonia-oxidation product gas, and having a temperature of 20° C. or less, in a methyl nitrite-recovering column, so as to convert nitrogen oxides contained in the purge gas and the ammonia-oxidation product gas to methyl nitrite and to absorb methyl nitrite contained in the purge gas and regenerated by the above-mentioned conversion, by methyl alcohol.

2. The process as claimed in claim 1, wherein the solid catalyst for the first step comprises a catalytic component comprising at least one member selected from the group consisting of platinum group metal elements and compounds of and a carrier for the catalytic component comprising at least one member selected from the group consisting of activated carbon, alumina, silica, diatomaceous earth, zeolite and clay minerals.

3. The process as claimed in claim 1, wherein the solid catalyst further comprises an assistant catalytic component comprising at least one member selected from the group consisting of copper compounds, iron compounds, bismuth compounds and cerium compounds.

4. The process as claimed in claim 1, wherein in the first step, carbon monoxide and methyl nitrite are diluted with an inert gas to form a feed gas, and in the feed gas, carbon monoxide is in a concentration of 1 to 50% by volume and methyl nitrite is in a concentration of 1 to 25% by volume.

5. The process as claimed in claim 1, wherein in the first step, the catalytic reaction is carried out at a temperature of 50° to 200° C. under a pressure of from 0 to 10 kg/cm$^2$G.

6. The process as claimed in claim 1, wherein in the second step, dimethyl oxalate is used in an amount of 3 to 10 times the weight of dimethyl carbonate introduced into the second step.

7. The process as claimed in claim 1, wherein the second step is carried out at a temperature of 0° to 100° C.

8. The process as claimed in claim 1, wherein in the second step, methyl alcohol is introduced into the dimethyl carbonate-absorbing column to recover dimethyl carbonate and dimethyl oxalate accompanying with the non-condensed gas, and the introduced methyl alcohol is in an amount of 5 to 30% by weight based on the weight of dimethyl carbonate introduced into the dimethyl carbonate-absorbing column.

9. The process as claimed in claim 1, wherein in the third step, the molecular oxygen-containing gas contains molecular oxygen in an amount of 0.08 to 0.2 mole per mole of nitrogen monoxide introduced into the methyl nitrite-regenerating column.

10. The process as claimed in claim 1, wherein in the third step, the contact of the non-condensed gas with the molecular oxygen-containing gas and methyl alcohol is carried out at a temperature of 60° C. or less.

11. The process as claimed in claim 1, wherein in the third step, the introduced methyl alcohol is in an amount of 2 to 5 moles per mole of nitrogen monoxide introduced into the methyl nitrite-regenerating column.

12. The process as claimed in claim 1, wherein the ammonia-oxidation product gas is produced by oxidizing ammonia with air and contains NOx compounds.

13. The process as claimed in claim 1, wherein the purge gas for the fifth step consists of a minor portion of the non-condensed gas withdrawn from the second step.

14. The process as claimed in claim 13, wherein the purge gas from the second step is fed into the recovering column of the fifth step in an amount of 0.1 to 30 volume %/hr, based on the total volume of the non-condensed gas fraction withdrawn from the absorbing column of the second step.

15. The process as claimed in claim 13, wherein the ammonia-oxidation product gas introduced into recovering column of the fifth step contains NOx compounds in an amount of 0.1 to 30 molar %/hr based on the total molar amount of methyl nitrite and nitrogen monoxide contained in the non-condensed gas fraction withdrawn from the absorbing column of the second step.

16. The process as claimed in claim 1, wherein the purge gas for the fifth step consists of a minor portion of the regenerated gas fraction withdrawn from the regenerating column of the third step.

17. The process as claimed in claim 16, wherein the purge gas from the third step is fed into the recovering column of the fifth step in an amount of 0.1 to 30 volume %/hr, based on the total volume of the regenerated gas fraction withdrawn from the regenerating column of the third step.

18. The process as claimed in claim 16, wherein the ammonia-oxidation product gas introduced into recovering column of the fifth step contains NOx compounds in an amount of 0.1 to 30 molar %/hr based on the total molar amount of methyl nitrite and nitrogen monoxide contained in the regenerated gas fraction withdrawn from the regenerating column of the third step.

19. The process as claimed in claim 1, wherein the methyl alcohol fractions containing methyl nitrite and provided in the fifth step are recycled to the methyl nitrite-regenerating column of the third step.

20. The process as claimed in claim 1, wherein in the fourth step, the absorbing medium fraction produced in the second step is subjected to a extract-distilling procedure to remove low boiling temperature compounds and then to a distilling procedure to collect dimethyl carbonate.

* * * * *